United States Patent
Amin et al.

(10) Patent No.: US 6,613,775 B1
(45) Date of Patent: Sep. 2, 2003

(54) IMIDAZO[1,2-A]PYRIDINE COMPOUNDS

(75) Inventors: Kosrat Amin, Mölndal (SE); Mikael Dahlström, Mölndal (SE); Peter Nordberg, Sävedalen (SE); Ingemar Starke, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/403,510

(22) PCT Filed: Aug. 18, 1999

(86) PCT No.: PCT/SE99/01401
§ 371 (c)(1),
(2), (4) Date: Oct. 22, 1999

(87) PCT Pub. No.: WO00/10999
PCT Pub. Date: Mar. 2, 2000

(30) Foreign Application Priority Data

Aug. 21, 1998 (SE) ................................................ 9802793

(51) Int. Cl.⁷ .................... A61K 31/437; C07D 471/04; A61P 1/04
(52) U.S. Cl. ........................................ 514/300; 546/121
(58) Field of Search ........................... 546/121; 514/300

(56) References Cited

U.S. PATENT DOCUMENTS

| | | | |
|---|---|---|---|
| 4,450,164 A | 5/1984 | Bristol et al. ................ | 424/256 |
| 4,725,601 A | 2/1988 | Ueda et al. ................... | 514/300 |

FOREIGN PATENT DOCUMENTS

| | | |
|---|---|---|
| EP | 0033094 | 8/1981 |
| EP | 0204285 | 12/1986 |

OTHER PUBLICATIONS

Bungaard H. Design of Prodrugs. Elsevier, Amsterdam–New York–Oxford. (1985). Chapter 1, pp. 1–3.*

Kaminski et al., Journal of Medicinal Chemistry, vol. 34, No. 2, 533–541, 1991.

Kaminski et al, Journal of Medicinal Chemistry, vol. 32, No. 8, 1686–1700, 1989.

Kaminski et al, Journal of Medicinal Chemistry, vol. 30, No. 11, 2047–2051, 1987.

Kaminski et al, Journal of Medicinal Chemistry, vol. 30, No. 11, 2031–2046, 1987.

Kaminski et al, Journal of Medicinal Chemistry, vol. 28, No. 7, 876–892, 1985.

* cited by examiner

*Primary Examiner*—Evelyn Mei Huang
(74) *Attorney, Agent, or Firm*—White & Case LLP

(57) ABSTRACT

The present invention relates to novel compounds, and therapeutically acceptable salts thereof of the formula (I), which inhibit exogenously or endogenously stimulated gastric acid secretion and thus can be used in the prevention and treatment of gastrointestinal inflammatory diseases.

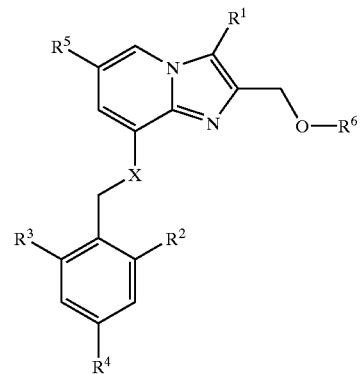

13 Claims, No Drawings

IMIDAZO[1,2-A]PYRIDINE COMPOUNDS

This application is a 371 of PCT/SE99/01401, filed on Aug. 18, 1999.

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); and from publications by J. J. Kaminski et al. in the Journal of Medical Chemistry (vol. 28, 876–892, 1985; vol. 30, 2031–2046, 1987; vol. 30, 2047–2051, 1987; vol. 32, 1686–1700, 1989; and vol. 34, 533–541, 1991).

For a review of the pharmacology of the gastric acid pump (the $H^+$, $K^+$-ATPase), see Sachs et al. (1995) Annu. Rev. Pharmacol. Toxicol. 35: 277–305.

DISCLOSURE OF THE INVENTION

It has surprisingly been found that compounds of the Formula I (I)

or a pharmaceutically acceptable salt thereof, are particularly effective as inhibitors of the gastrointestinal $H^+$, $K^+$-ATPase and thereby as inhibitors of gastric acid secretion.

In one aspect, the invention thus relates to compounds of the general Formula I (I)

or a pharmaceutically acceptable salt thereof, wherein $R_1$ is
  (a) H,
  (b) $CH_3$, or
  (c) $CH_2OH$;

$R^2$ is $C_1-C_6$ alkyl;

$R^3$ is $C_1-C_6$ alkyl;

$R^4$ is
  (a) H, or
  (b) halogen;

$R^5$ is
  (a) H, or
  (b) $C_1-C_6$ alkyl;

$R^6$ is
  (a) H,
  (b) $C_1-C_6$ alkyl carbonyl
  (c) $C_3-C_7$ cycloalkyl carbonyl, in which the cycloalkyl group is optionally substituted by one or more substituents selected from, $C_1-C_6$ alkyl, $C_1-C_6$ alkoxy, —COOH or —COO—($C_1-C_6$)alkyl
  (d) Aryl $C_1-C_6$ alkyl carbonyl, in which aryl represents phenyl, pyridyl, thienyl or furanyl, optionally substituted by one or more substituents selected from, $C_1-C_6$ alkyl, $C_1-C_6$ alkoxy, —COOH or —COO—($C_1-C_6$)alkyl
  (e) $C_1-C_6$ alkoxy $C_1-C_6$ alkyl carbonyl
  (f) $C_1-C_6$ alkoxy carbonyl
  (g) aryl carbonyl, in which aryl represents phenyl, pyridyl, thienyl or furanyl, optionally substituted by one or more substituents selected from, $C_1-C_6$ alkyl, $C_1-C_6$ alkoxy, —COOH or —COO—($C_1-C_6$)alkyl
  (h) $C_3-C_7$ cycloalkyl $C_1-C_6$ alkylcarbonyl, in which the cycloalkyl group is optionally substituted by one or more substituents selected from, $C_1-C_6$ alkyl, $C_1-C_6$ alkoxy, —COOH or —COO—($C_1-C_6$)alkyl
  (i) $C_1-C_6$ alkoxy $C_1-C_6$ alkoxycarbonyl
  (j) $C_1-C_6$ alkoxy $C_1-C_6$ alkoxy $C_1-C_6$ alkylcarbonyl
  (k) acarbamoylgroup with the formula wherein $R^7$ and $R^8$ are the same or different and are H, or $C_1-C_6$ alkyl
  (l) $R^9$—($C_1-C_6$)alkylcarbonyl
  wherein $R^9$ is HOC=O—, $C_1$–$C_6$ alkyl-O—C=O—, or
an amino group with the formula

wherein $R^7$ and $R^8$ are the same or different and are H, or $C_1$–$C_6$ alkyl
(m) $R^9$-hydroxylated-($C_1$–$C_6$)alkylcarbonyl
(n) $R^9$—($C_1$–$C_6$)alkenylcarbonyl
X is
(a) NH, or
(b) O.

As used herein, the term "$C_1$–$C_6$ alkyl" denotes a straight or branched alkyl group having from 1 to 6 carbon atoms. Examples of said $C_1$–$C_6$ alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

The term "pyridyl" includes the 2-, 3-, and 4-isomers and the terms thienyl and furanyl include the 2-, and 3-isomers.

Both the pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitable therapeutically acceptable salts. Examples of such acids are hydrohalogen acids such as hydrochloric acid, sulphuric acid, phosphoric acid, nitric acid, aliphatic, alicyclic, aromatic or heterocyclic carboxyl or sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halogenbenzenesulphonic acid, toluenesulphonic acid or naphthalenesulphonic acid.

Preferred compounds according to the invention are those of Formula I wherein $R^1$ is $CH_3$ or $CH_2OH$; $R^2$ is $CH_3$ or $CH_2CH_3$; $R^3$ is $CH_3$ or $CH_2CH_3$; $R^4$ is H, Br, Cl or F; $R^5$ is H or $CH_3$.

Particularly preferred compounds according to the invention are:

8-(2,6-dimethylbenzylamino)-2-hydroxymethyl-3-methylimidazo[1,2-a]pyridine 8-(2-ethyl-6-methylbenzylamino)-2-hydroxymethyl-3-methylimidazo[1,2-a]pyridine 8-(2,6-dimethylbenzylamino)-3,6-dimethyl-2-hydroxymethylimidazo[1,2-a]pyridine

[8-(2,6-dimethylbenzylamino)-3-methylimidazo[1,2-a]pyridin-2-yl]methyl acetate

[8-(2,6-dimethylbenzylamino)-3-methylimidazo[1,2-a]pyridin-2-yl]methyl ethyl carbonate

[8-(2,6-dimethylbenzylamino)-3-methylimidazo[1,2-a]pyridin-2-yl]methyl N,N-dimethylcarbamate 1-[[8-(2,6-dimethylbenzylamino)-3-methylimidazo[1,2-a]pyridin-2-yl]methyl]3-ethyl malonate 4-[[8-(2,6-dimethylbenzylamino)-3-methylimidazo[1,2-a]pyridin-2-yl]methoxy]-4-oxobutanoic acid 4-[[8-(2-ethyl-6-methylbenzylamino)-3-methylimidazo[1,2-a]pyridin-2-yl]methoxy]-4-oxobutanoic acid 5-[[8-(2,6-dimethylbenzylamino)-3-methylimidazo[1,2-a]pyridin-2-yl]methoxy]-5-oxopentanoic acid

[8-(2,6-dimethylbenzylamino)-3-methylimidazo[1,2-a]pyridin-2-yl]methyl 2-(dimethylamino)acetate 8-(2,6-dimethylbenzylamino)-2,3-dihydroxymethyl-imidazo[1,2-a]pyridine Preparation The present invention also provides the following processes A and B for the manufacture of compounds with the general Formula I.

The process A for manufacture of compounds with the general Formula I comprises the following steps:

a) The imidazo[1,2-a]pyridine compounds of the Formula II

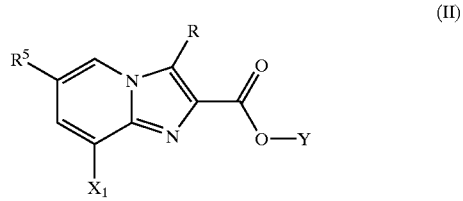

wherein Y is a lower alkyl group, R represents H, $CH_3$ or an ester group such as $COOCH_3$, $COOC_2H_5$ etc, $X_1$ is $NH_2$ or OH and $R^5$ is as defined for Formula I, can be prepared by reacting compounds of the general Formula III

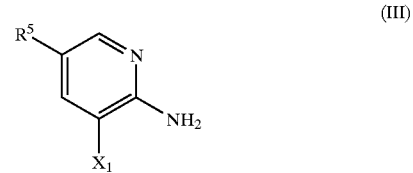

with compounds of the general Formula IV

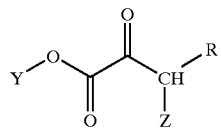

(IV)

wherein Z is a leaving group such as halogen, mesyl, or tosyl.

The reaction is carried out under standard conditions in an inert solvent such as acetone acetonitrile, alcohol, N,N-dimethylformamide etc., with or without a base.

b) Compounds of the Formula II can be reacted with compounds of the Formula V

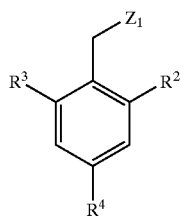

(V)

wherein $R^2$, $R^3$ and $R^4$ are as defined for Formula I and $Z_1$ is a leaving group, such as halogen, tosyl or mesyl, under standard conditions in an inert solvent, with or without a base, to compounds of Formula VI

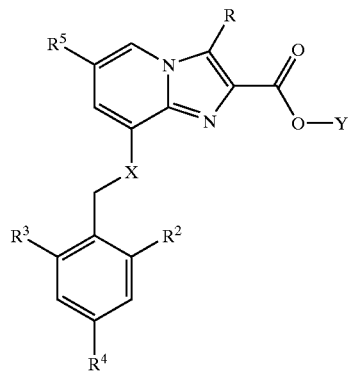

(VI)

wherein $R^2$, $R^3$, $R^4$, $R^5$ and X are as defined for Formula I, Y is a lower alkyl group and R is H, $CH_3$ or an ester group such as $COOCH_3$, $COOC_2H_5$ e.t.c.

c) Reduction of compounds of the general Formula VI e.g. by using lithium aluminium hydride or Red-Al® in ahn inert solvent such as tetrahydrofuran, ether or toluene yields the compounds of the general Formula I wherein $R^6$ is H.

d) The substituent $R^6$ of Formula I ($R^6{\neq}H$) can be introduced by standard acylating procedures carried out under standard conditions, eg. by reacting compounds of Formula I, wherein $R^6$ is H, with the acid, acid halide or the anhydride of $R^6$ ($R^6{\neq}H$).

The process B for manufacture of compounds with the general Formula I comprises the following steps:

a) In compounds of Formula I wherein $R^6$ is H, the hydroxymethyl group can be halogenated by standard methods in an inert solvent, to the corresponding halogenmethyl group of Formula VII

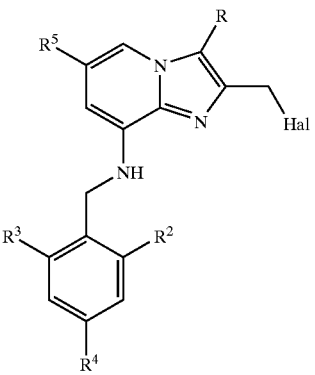

(VII)

b) The substituent $R^6$ of Formula I ($R^6{\neq}H$) can be introduced by reacting compounds of Formula VII with the corresponding acid of $R^6$ ($R^6{\neq}H$). The reaction is carried out under standard conditions in an inert solvent with or without a base.

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre-and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics such as amoxicillin.

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention, vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The compounds according to the invention can also be used in formulations together with other active ingredients, e.g. for the treatment or prophylaxis of conditions involving infection by *Helicobacter pytori* of human gastric mucosa. Such other active ingredients may be antimicrobial agents, in particular:

β-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

The compounds according to the present invention can also be used together or in comibination for simultaneous, separate or sequential use with antacids such as aluminum hydroxide, magnesium carbonate and magnesium hydroxid or alginic acid, or together or in combination for simultaneous, separate or sequential use with pharmaceuticals which inhibit acid secretion, such as, H2-blockers (e.g cimetidine, ranitidine), $H^+/K^+$-ATPase inhibitors (e.g. omeprazole, pantoprazole, lansoprazole or rabeprazole), or together or in combination for simultaneous, separate or sequential use with gastroprokinetics (e.g. cisapride or mosapride).

EXAMPLES

1. PREPARATION OF COMPOUNDS OF THE INVENTION

Example 1.1

Synthesis of 8-(2,6-Dimethylbenzylamino)-2-hydroxymethyl-3-methylimidazo[1,2-a]pyridine

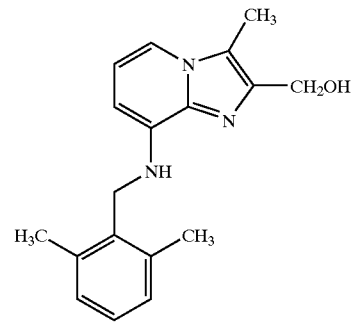

Ethyl 8-(2,6-dimethylbenzylamino)-3-methylimidazo[1,2-a]pyridin-2-carboxylate (5.2 g, 0.015 mol) was solved in tetrahydrofuran (100 ml) and LiAlH4 (1.15 g 0.03 mol) was added. After stirring the mixture at room temperature for 45 min, 1.15 ml of water was added dropwise, followed by 1.15 ml of 15% sodium hydroxide and then 3.45 ml of water. The solids were removed by filtration and washed thoroughly with methylene chloride. The filtrate and washings were combined and dried and the solvents were removed under reduced-pressure. Purification of the residue by column chromatography on silica gel using methylene chloride : methanol (10:2) as eluent gave 3.2 g (73%) of the title compound.

$^1$H-NMR (300 MHz, DMSO-$d_6$): δ 2.35 (s, 6H), 2.4 (s, 3H), 4.35 (d, 2H), 4.5 (d, 2H), 4.85 (t, 1H), 4.9 (t, 1H), 6.3 (s, 1H), 6.8 (t, 1H), 7.05–7.2 (m, 3H), 7.55 (d, 1H)

Example 1.2

Synthesis of 8-(2-Ethyl-6-methylbenzylamino)-2-hydroxymethyl-3-methylimidazo[1,2-a]pyridine

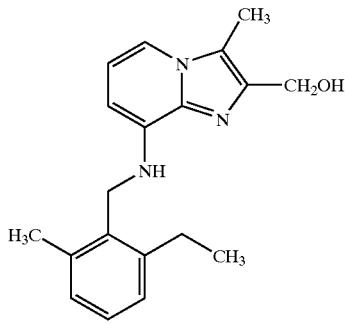

To a suspension of LiAlH$_4$ (0.24 g, 6.4 mmol) in anhydrous tetrahydrofuran (25 ml) in an argon atmosphere was added dropwise during 30 min. ethyl 8-(2-ethyl-6-dimetylbenzylamino)-3-methylimidazo[1,2-a]pyridin-2-carboxylate (1.1 g, 3.2 mmol) dissolved in anhydrous tetrahydrofuran (25 ml). After stirring the mixture at room temperature for 4 h, 0.24 ml of water was added dropwise, followed by 0.24 ml of 15% sodium hydroxide and then 0.75 ml of water. The solids were removed by filtration and washed thoroughly with tetrahydrofuran and methylene chloride: methanol (9:1). The filtrate and washings were combined and dried and the solvents were removed under reduced pressure. The residue was purified by column chromatography on silica gel using methylene chloride: methanol (9:1) as eluent. Treating the residue with acetonitrile and filtration gave 0.76 g (77%) of the title compound.

$^1$H-NMR (300 MHz, CDCl$_3$): δ 1.2 (t, 3H), 2.3 (s, 3H), 2.4 (s, 3H), 2.75 (q, 2H), 4.35 (d, 2H), 4.45 (s, 2H), 4.75 (bs, 1H), 5.45 (t, 1H), 6.2 (d, 1H), 6.75 (t, 1H), 7.05–7.25 (m, 4H)

Example 1.3

Synthesis of 8-(2,6-Dimethylbenzylamino)-3,6-dimethyl-2-hydroxymethylimidazo[1,2-a]pyridine

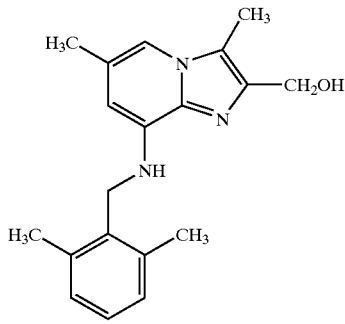

To a suspension of LiAlH$_4$ (0.19 g, 5.1 mmol) in anhydrous tetrahydrofuran (15 ml) in an argon atmosphere was added dropwise during 30 min ethyl 8-(2-ethyl-6-dimethylbenzylamino)-3,6-dimethylimidazo[1,2-a]pyridin-2-carboxylate (0.9 g, 2.6 mmol) solved in anhydrous tetrahydrofuran (15 ml). After stirring the mixture at room temperature for 2 h, 0.2 ml of water was added dropwise, followed by 0.2 ml of 15% sodium hydroxide and then 0.6 ml of water. The solids were removed by filtration and washed thoroughly with methylene chloride: methanol (1:1).

The filtrate and washings were combined and dried and the solvents were removed under reduced pressure. The residue was purified by column chromatography on silica gel using methylene chloride: methanol (9:1) as eluent. Treating the residue with acetonitrile and filtration gave 0.36 g (77%) of the title compound.

$^1$H-NMR (300 MHz, CDCl$_3$): δ 2.35 (s, 6H), 2.4 (s, 6H), 4.35 (d, 2H), 4.45 (s, 2H), 5.25 (t, 1H), 6.1 (s, 1H), 7.0–7.2 (m, 4H).

Example 1.4

Synthesis of [8-(2,6-Dimethylbenzylamino)-3-methylimidazo[1,2-a]pyridin-2-yl]methyl Acetate

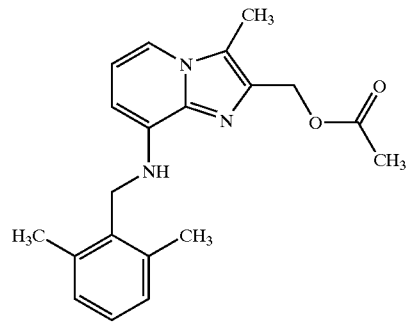

To a solution of 8-(2,6-dimethylbenzylamino)-2-hydroxymethyl-3-methylimidazo[1,2-a]pyridine (0.3 g, 1.0 mmol) and triethylamine (0.014 ml, 1.0 mmol) in methylene chloride (10 ml) was added dropwise acetyl chloride (0.071 ml, 1.0 mmol). The reaction mixture was stirred for 1.5 h. at room temperature. Water was added and the organic layer was separated, washed with sodium bicarbonate solution, dried (Na$_2$SO$_4$) and evaporated under reduced pressure. The residue was purified by column chromatography on silica gel using diethyl ether as eluent. Recrystallization from diethyl ether gave 0.16 g (47%) of the desired product.

$^1$H-NMR (300 MHz, CDCl$_3$): δ 2.05 (s, 3H), 2.4 (s, 6H), 2.45 (s, 3H), 4.35 (d, 2H), 4.95 (bs, 1H), 5.2 (s, 2H), 6.25 (d, 1H), 6.8 (t, 1H), 7.05–7.2 (m, 3H), 7.3 (d, 2H).

Example 1.5

Synthesis of [8-(2,6-Dimethylbenzylamino)-3-meihylimidazo[1,2-a]pyridin-2-yl]methyl Ethyl Carbonate

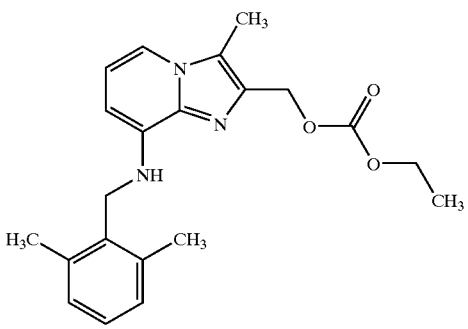

8-(2,6-dimethylbenzylamino)-2-hydroxymethyl-3-methylimidazo[1,2-a]pyridine (0.4 g, 1.3 mmol) and ethyl chloroformate (0.13 ml, 1.3 mmol) were solved in methylene chloride (20 ml) and were refluxed for 3 h. An additional amount of ethyl chloroformate (0.13 ml, 1.3 mmol) was added and the reaction mixture was refuxed 20 h. A sodium bicarbonate solution was added, the organic layer was separated dried ($Na_2SO_4$) and evaporated under reduced pressure. Purification of the residue by column chromatography on silica gel using diethyl ether as eluent and crystallization from diethyl ether: petroleum ether (1:2) gave 0.11 g (23%) of the title compound.

$^1$H-NMR (300 MHz, $CDCl_3$): δ 1.25 (t, 1H), 2.4 (s, 6H), 2.5 (s, 3H), 4.15 (q, 2H), 4.35 (d, 2H), 4.95 (bs, 1H), 5.25 (2H), 6.25 (d, 1H), 6.8 (t, 1H), 7.05–7.2 (m, 3H), 7.3 (d, 1H).

Example 1.6

Synthesis of [8-(2,6-Dimethylbenzylamino)-3-methylimidazo[1,2-a]pyridin-2-y]ymethyl N,N-dimethylcarbamate

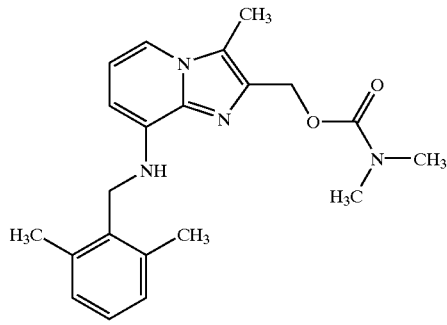

8-(2,6-dimethylbenzylamino)-2-hydroxymethyl-3-methylimidazo[1,2-a]pyridine (0.1 g, 0.34 mmol), dimethylcarbamyl chloride (0.03 ml, 0.34 mmol), sodium carbonate (0.1 g, 0.94 mmol) and a cat. amount of N,N-dimethylaminopyridine were added to acetonitrile (15 ml) and refluxed for 20 h. An additional amount of dimethylcarbamyl chloride (0.15 ml, 1.7 mmol) was added and the reaction mixture was refluxed for 24 h. The solids were removed by filtration and the solvent was evaporated under reduced pressure. The residue was purified by column chromatography on silica gel using ethyl acetate: petroleum ether (2:1) as eluent gave 0.07 g (56%) of the title compound.

$^1$H-NMR (300 MHz, $CDCl_3$): δ 2.4 (s, 6H), 2.5 (s, 3H), 2.85 (d, 6H), 4.35 (d, 2H), 4.9 (bs, 1H), 5.2 (s, 2H), 6.25 (d, 1H), 6.75 (t, 1H), 7.05–7.15 (m, 3H), 7.3 (d, 1H).

Example 1.7

Synthesis of 1-[[8-(2,6-Dimethylbenzylamino)-3-methylimidazo[1,2-a]pyridin-2-y]methyl]3-ethyl Malonate

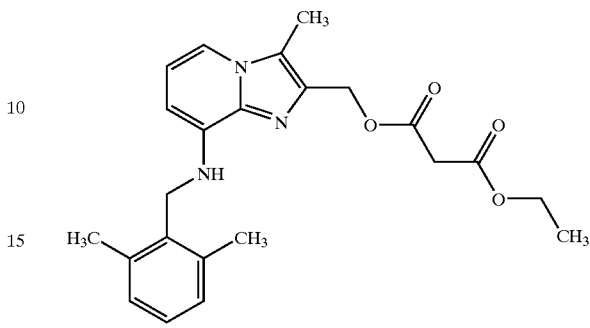

8-(2,6-dimethylbenzylamino)-2-hydroxymethyl-3-methylimidazo[1,2-a]pyridine (0.45 g, 1.5 mmol), ethyl malonyl chloride (0.23 g, 1.5 mmol) and sodium carbonate (0.32 g, 3.0 mmol) were added to methylene chloride (20 ml) and the mixture was stirred for 3 h. at room temperature. Water was added and the organic layer was separated, dried ($Na_2SO_4$) and evaporated under reduced pressure. Purification of the residue by column chromatography on silica gel using diethyl ether as eluent and crystallization from petroleum ether gave 0.34 g (56%) of the desired product.

$^1$H-NMR (300 MHz, $CDCl_3$): δ 1.2 (t, 3H), 2.4 (s, 6H), 2.55 (s, 3H), 3.4 (s, 2H), 4.15 (q, 2H), 4.35 (d, 2H), 4.9 (t, 1H), 5.25 (s, 2H), 6.25 (d, 1H), 6.8 (t, 1H), 7.05–7.15 (m, 3H), 7.35 (d, 1H).

Example 1.8

Synthesis of 4-[[8-(2,6-Dimethylbenzylamino)-3-methylimidazo[1,2-a]pyridin-2-yl]methoxy]-4-oxobutanoic Acid

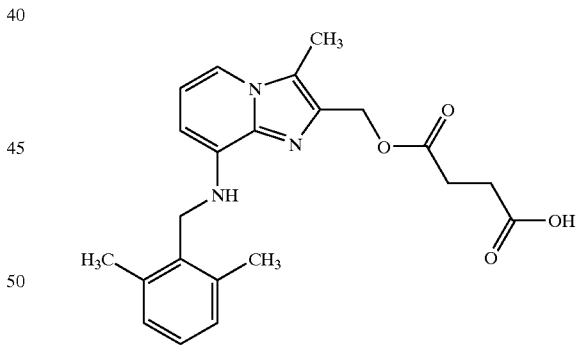

To a suspension of 8-(2,6-dimethylbenzylamino)-2-hydroxymethyl-3-methylimidazo[1,2-a]pyridine (0.2 g, 0.68 mmol) in acetonitrile (10 ml) was added sodium hydride (50% in oil) (0.036 g, 0.75 mmol) and the mixture was stirred for 5 min. To the mixture was added succinic anhydride (0.1 g, 1.0 mmol) and the reaction mixture was refluxed for 20 h. The solvent was evaporated under reduced pressure. To the residue was added water and the solid that formed was isolated by filtration and washed with acetonitrile to give 0.24 g (89%) of the title compound.

$^1$H-NMR (300 MHz, $CDCl_3$): δ 2.35–2.55 (m, 13H), 4.35 (s, 2H), 4.9 (bs, 2H), 5.2 (s, 2H) 6.25 (d, 1H), 6.8 (t, 1H), 7.0–7.1 (m, 3H), 7.25 (d, 1H).

Example 1.9

Synthesis of 4-[[8-(2-Ethyl-6-methylbenzylamino)-3-methylimidazo[1,2-a]pyridin-2-yl]methoxy]-4-oxobutanoic Acid

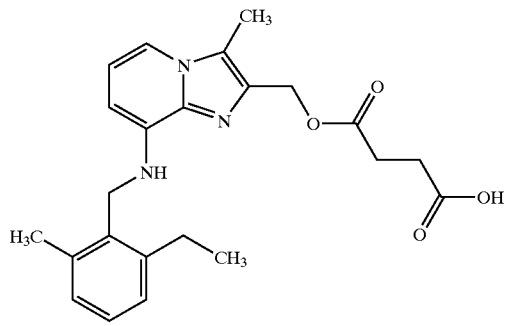

To a suspension of 8-(2-ethyl-6-methylbenzylamino)-2-hydroxymethyl-3-methylimidazo[1,2-a]pyridine (0.47 g, 1.5 mmol) in acetonitrile (20 ml) was added sodium hydride (50% in oil) (0.081 g, 1.7 mmol) and the mixture was stirred for 5 min. To the mixture was added succinic anhydride (0.23 g, 2.3 mmol) and the reaction mixture was refluxed for 20 h. The solvent was evaporated under reduced pressure. The residue was suspended in water and the pH was adjusted to 6 with 2M HCl and the solid that formed was isolated by centrifuging. Washing with water and with acetonitrile gave 0.51 g, (82%) of the desired product.

$^1$H-NMR (300 MHz, CDCl$_3$): δ 1.2 (t, 1H), 2.35–2.55 (m, 10H), 2.7 (q, 2H), 4.3 (s, 2H), 5.2 (s, 2H), 6.25 (d, 1H), 6.8 (t, 1H), 7.0–7.2 (m, 3H), 7.3 (d, 1H).

Example 1.10

Synthesis of 5-[[8-(2,6-Dimethylbenzylamino)-3-methylimidazo[1,2-a]pyridin-2-yl]methoxy]-5-oxopentanoic Acid

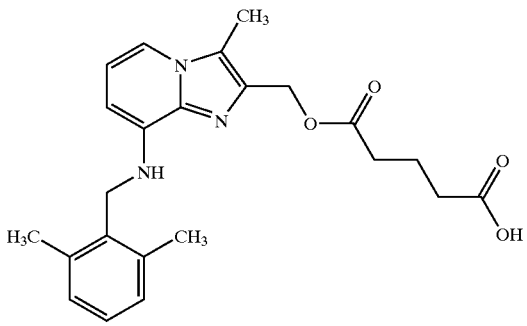

To a solution of 8-(2,6-dimethylbenzylamino)-2-hydroxymethyl-3-methylimidazo[1,2-a]pyridine (0.3 g, 1.0 mmol) in tetrahydrofuran(10 ml) was added sodium hydride (50% in oil) (0.054 g, 1.1 mmol) and the mixture was stirred for 10 min. To the mixture was added glutaric anhydride (0.13 g, 1.1 mmol) and the reaction mixture was refluxed for 20 h. The solvent was evaporated under reduced pressure. The residue was partitioned between dichloromethane and water. The pH was adjusted to 4 with 2M HCl. The organic layer was separated, dried (Na$_2$SO$_4$) and evaporated under reduced pressure. Purification of the residue by column chromatography on silica gel using dichloromethane:methanol (94:6) as eluent gave 0.034 g (8%) of the title compound.

$^1$H-NMR (300 MHz, CDCl$_3$): δ 1.75 (t, 2H), 2.1 (t, 2H), 2.3 (t, 2H), 2.35 (s, 6H), 2.45 (s, 3H), 4.3 (s, 2H), 5.2 (s, 2H), 5.5 (bs, 1H), 6.25 (d, 1H), 6.8 (t, 1H), 7.0–7.15 (m, 3H), 7.3 (d, 1H).

Example 1.11

Synthesis of [8-(2,6-Dimethylbenzylamino)-3-methylimidazo[1,2-a]pyridin-2-yl]methyl 2-(dimethylamino)acetate

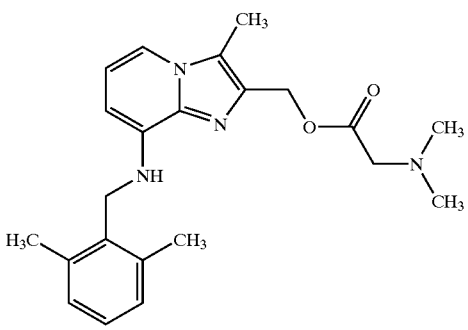

8-(2,6-dimethylbenzylamino)-2-chloromethyl-3-methylimidazo[1,2-a]pyridine (0.3 g, 1.0 mmol) and N,N-dimethylglycine (0.1 g, 1.0 mmol) were added to acetonitrile (10 ml) and the mixture was refluxed for 20 h. The solvent was evaporated under reduced pressure and the residue was purified by column chromatography on silica gel using, dichloromethane:methanol (10:2) as eluent. Recrystallization from acetonitrile gave 0.12 g (32%) of the title compound.

$^1$H-NMR (3060 MHz, CD$_3$OD): δ 2.4 (s, 6H) 2.55 (s, 3H), 3.25 (s, 6H), 3.85 (s, 2H), 4.4 (s, 2H), 4.9 (s, 2H), 6.5 (d, 1H), 6.95 (t, 1H), 7.05–7.15 (m, 3H), 7.6 (d, 1H).

Example 1.12

Synthesis of 8-(2,6-Dimethylbenzylamino)-2,3-dihydroxymethyl-imidazo[1,2-a]pyridine

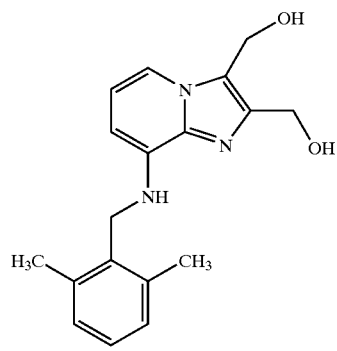

To an ice cooled solution of diethyl 8-(2,6-dimethylbenzylamino)imidazo[1,2-a]pyridine-2,3-dicarboxylate (2.5 g, 6.3 mmol) in toluene (100 ml) was added Red-Al (14 ml, 45 mmol)(65% in toluene) during 3 h. The temperature was allowed to rise to room temperature and a Rochell salt solution (35 g potassium sodium tartrate in 250 ml H2O) was added. The organic layer was separated dried and evaporated under reduced pressure. Purification of the residue by column chromatography on silica gel using dichloromethane: isopropylalcohol (4:1) gave 0.09 g (5%) of de desired product.

$^1$H-NMR (300 MHz, CDCl$_3$): δ 2.4 (s, 6H), 4.45 (s, 2H), 4.7 (s, 2H), 4.95 (s, 2H), 6.5 (d, 1H), 6.9 (t, 1H), 7.05–7.2 (m, 3H), 7.75 (d, 1H).

2. PREPARATION OF INTERMEDIATES

Example 2.1

Synthesis of ethyl 8-Amino-3-methylimidazo[1,2-a]pyridin-2-carboxylate

A solution of 2,3-diaminopyridine (6.8 g, 62 mmol) and 3-bromo-2-oxo-butyric acid ethyl ester (13 g, 62 mmol) in 1,2-dimethoxyethane (150 ml) was refluxed for 2 h. Sodium carbonate (6.5 g, 62 mmol) was added and the mixture was refluxed for 2 h. The solids were isolated by filtration and washed with dichloromethane:methanol (10:1). The filtrate and washings were combined the solvents were removed under reduced pressure. The oily residue was washed with petroleum ether and was purified twice by column chromatography on silica gel using 1) dichloromethane:methanol (10:1) 2) ethyl acetate as eluent to give 4.6 g (34%) of the title compound.

$^1$H-NMR (300 MHz, CDCl$_3$): δ 1.45 (t, 3H), 2.75 (s, 1H), 4.5 (q, 2H), 4.65 (bs, 2H), 6.35 (d, 1H), 6.7 (t, 1H), 7.35 (d, 1H).

Example 2.2

Synthesis of ethyl 8-(2,6-Dimethylbenzylamino)-3-methylimidazo[1,2-a]pyridin-2-carboxylate Ethyl 8-amino-3-methylimidazo[1,2-a]pyridin-2-carboxylate (4.6 g, 21 mmol), 2,6-dimethylbenzyl chloride (3.2 g, 21 mmol), sodium carbonate (4.4 g, 42 mmol) and a cat amount of potassium iodide were added to acetonitrile (50 ml) and refluxed for 3 h., stirred for 20 h. at room temperature and refluxed for 1 h. The solids were removed by filtration and the solvents were evaporated under reduced pressure. The residue was dissolved in methylene chloride and washed with water. The organic layer was separated, dried (Na$_2$SO$_4$) and evaporated under reduced pressure. Purification of the residue by column chromatography on silica gel using methylene chloride:methanol (10:1) as eluent and crystallization from ethyl acetate gave 4.0 g (56%) of the desired product.

$^1$H-NMR (300 MHz, CDCl$_3$): δ 1.4 (t, 3H), 2.4 (s, 6H), 2.75 (s, 3H), 4.35 (d, 2H), 4.45 (q, 2H), 5.15 (t, 1H), 6.25 (d, 1H), 6.85 (t, 1H), 7.05–7.2 (m, 3H), 7.35 (d, 1H).

Example 2.3

Synthesis of ethyl 8-(2-Ethyl-6-methylbenzylamino)-3-methylimidazo[1,2-a]pyridin-2-carboxylate To a stirred mixture of ethyl 8-amino-3-methylimidazo[1,2-a]pyridin-2-carboxylate (1.53 g, 7.0 mmol) in methanol (25 ml) were added 2-ethyl-6-methylbenzaldehyde (1.1 g, 7.1 mmol), zinc(II)chloride (1.1 g, 8.0 mmol) in methanol (10 ml) and sodium cyanoborohydride (0.5 g, 8.0 mmol). The reaction mixture was refluxed for 4 h. and then stirred at room temperature for 20 h. Triethylamine (2.5 ml) was added and the mixture was stirred for 30 min. and evaporated under reduced pressure. Purification of the residue by column chromatography twice on silica gel using 1) methylene chloride:methanol (95:5) 2) heptane:isopropyl ether (1:5) as eluent gave 0.2 g (8%) of the title compound.

$^1$H-NMR (300 MHz, CDCl$_3$): δ 1.25 (t, 3H), 1.4 (t, 3H), 2.4 (s, 3H), 2.65–2.8 (m, 5H), 4.35 (d, 2H), 4.45 (q, 2H), 5.15 (t, 1H), 6.25 (d, 1H), 6.85 (t, 1H), 7.05–7.2 (m, 3H), 7.35 (d, 1H).

Example 2.4

Synthesis of Ethyl 8-Amino-3,6-dimethylimidazo[1,2-a]pyridin-2-carboxylate

A solution of 2,3-diamino-5-methyl-pyridine (2.3 g, 19 mmol) and 3-bromo-2-oxo-butyric acid ethyl ester (4.3 g, 21 mmol) in ethanol (25 ml) was refluxed for 20 h. Sodium carbonate (2.6 g, 25 mmol) was added and the mixture was filtrated and the solids were washed with ethanol. The filtrate and washings were combined and evaporated under reduced pressure. The residue was dissolved in methylene chloride, washed twice with a sodium carbonate solution and twice with water. The organic layer was separated dried (Na$_2$SO$_4$) and evaporated under reduced pressure. Purification of the residue by column chromatography on silica gel using methylene chloride:methanol (9:1) as eluent gave 1.3 g (30%) of the title compound as an oil.

$^1$H-NMR (300 MHz, CDCl$_3$): δ 1.4 (t, 3H), 2.25 (s, 3H), 2.7 (s, 3H), 4.45 (q, 2H), 4.75 (bs, 2H), 6.2 (s, 1H), 7.1 (s, 1H).

Example 2.5

Synthesis of Ethyl 8-(2,6-Dimethylbenzylamino)-3,6-dimethylimidazo[1,2-a]pyridin-2-carboxylate Ethyl 8-amino-3,6-dimethylimidazo[1,2-a]pyridin-2-carboxylate (1.3 g, 5.6 mmol), 2,6-dimethylbenzyl chloride (0.9 g, 6.2 mmol), potassium carbonate (1.5 g, 11 mmol) and sodium iodide (0.1 g, 0.6 mmol) were added to acetonitrile (15 ml) and refluxed for 20 h. The solvent was evaporated under reduced pressure. The residue was dissolved in methylene chloride , washed twice with water and the organic layer was separated dried (Na$_2$SO$_4$) and evaporated under reduced pressure. Purification of the residue by column chromatography on silica gel using heptane:ethyl acetate (2:1) as eluent gave 0.9 g (47%) of the title compound as an oil.

$^1$H-NMR (300 MHz, CDCl$_3$): δ 1.35 (t, 3H), 2.4 (s, 3H), 2.45 (s, 6H), 2.7 (s, 3H), 4.35 (d, 2H), 4.4 (q, 2H), 5.05 (t, 1H), 6.1 (s, 1H), 7.05–7.2 (m, 4H).

Example 2.6

Synthesis of Diethyl 8-Aminoimidazo[1,2-a]pyridin-2 3-dicarboxylate

A solution of 2,3-diaminopyridine (13.1 g, 0.12 mol), 2-bromo-3-oxo-succinic acid diethyl ester (31 g, 0.12 mol) and sodium carbonate (13.2 g, 0.12 mol) in 1,2-dimethoxyethane (200 ml) was refluxed for 20 h. The solvent was evaporated under reduced pressure and the residue was suspended in methylene chloride and filtrated through silica gel. The filtrate was evaporated under reduced pressure to give 10.9 g (33%) of the title compound as an oil.

$^1$H-NMR (300 MHz, CD3OD): δ 1.5 (t, 6H), 4.5 (q, 4H), 7.15 (d, 1H), 7.3 (t, 1H), 8.75 (d, 1H).

Example 2.7

Synthesis of Diethyl 8-(2, 6-Dimethylbenzylamino)-imidazo[1,2-a]pyridin-2,3-dicarboxylate Diethyl 8-aminoimidazo[1,2-a]pyridin-2,3-dicarboxylate (2.8 g, 10 mmol), 2,6-dimethylbenzyl chloride (1.9 g, 12 mmol), potassium carbonate (2.0 g, 15 mmol) and sodium iodide (0.22 g, 1.5 mmol) were added to acetonitrile (100 ml) and refluxed for 20 h.

Methylene chloride was added to the cooled reaction mixture and was washed with water. The organic layer was separated, dried ($Na_2SO_4$) and evaporated under reduced pressure. Purification of the residue by column chromatography on silica gel using methylene chloride as eluent gave 2.5 g (63%) of the title compound.

$^1$H-NMR (300 MHz, $CDCl_3$): δ 1.3–1.45 (m, 6H), 2.35 (s, 6H), 4.3 (d, 2H), 4.35–4.45 (m, 4H), 5.05 (t, 1H), 6.45 (d, 1H), 6.95–7.15 (m, 4H), 8.55 (d, 1H).

Example 2.8

Synthesis of 8-(2,6-Dimethylbenzylamino)-2-chloromethyl-3-methylim idazo[1,2-a]pyridine To a solution of 8-(2,6-dimethylbenzylamino)-2-hydroxymethyl-3-methylimidazo[1,2-a]pyridine (1.0 g, 3.4 mmol) in methylene chloride (50 ml) was added dropwise thionyl chloride (0.5 g, 3.4 mmol) solved in methylene chloride (10 ml) at 5° C. The reaction mixture was stirred 2 h. at 5° C. To the mixture was washed with a saturated bicarbonate solution, the organic layer was separated, dried ($Na_2SO_4$) and evaporated under reduced pressure to give 1.0 g (93%) of the title compound.

$^1$H-NMR (300 MHz, $CDCl_3$): δ 2.4 (s, 6H), 2.5 (s, 3H), 4.35 (d, 2H), 4.75 (s, 2H), 4.9 (bs, 1H), 6.25 (d, 1H), 6.8 (t, 1H), 7.05–7.15 (m, 3H), 7.25 (d, 1H).

BIOLOGICAL TESTS

1. In vitro Experiments

Acid Secretion Inhibition in Isolated Rabbit Gastric Glands

Inhibiting effect on acid secretion in vitro in isolated rabbit gastric glands was measured as described by Berglindh et al. (1976) Acta Physiol. Scand. 97, 401–414.

Determination of $H^+,K^+$-ATPase Activity

Membrane vesicles (2.5 to 5 µg) were incubated for 15 min at +37° C. in 18 mM Pipesfrris buffer pH 7.4 containing 2 mM $MgCl_2$, 10 nM KCl and 2 mM ATP. The ATPase activity was estimated as release of inorganic phosphate from ATP, as described by LeBel et al. (1978) Anal. Biochem. 85, 86–89.

2. In vivo Experiments

Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg·h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F%) following intraduodenal or oral administration is calculated as F(%)= (AUC (p.o. or i.d.)/AUC (i.v.))×100.

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F %) after oral or i.d. administration is calculated as described above in the rat model.

What is claimed is:

1. A compound of Formula I

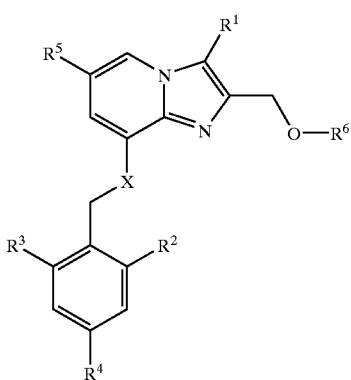

(I)

or a pharmaceutically acceptable salt thereof, wherein
$R^1$ is selected from the group consisting of:
(a) H,
(b) $CH_3$, and
(c) $CH_2OH$;
$R^2$ is $C_1-C_6$ alkyl;
$R^3$ is $C_1-C_6$ alkyl;
$R^4$ is selected from the group consisting of:
(a) H and
(b) halogen;
$R^5$ is selected from the group consisting of:
(a) H and
(b) $C_1-C_6$ alkyl;
$R^6$ is selected from the group consisting of:
(a) H,
(b) $C_1-C_6$ alkyl carbonyl,
(c) $C_3-C_7$ cycloalkyl carbonyl, wherein the cycloalkyl group is optionally substituted by one or more substituents selected from the group consisting of $C_1-C_6$ alkyl, $C_1-C_6$ alkoxy, —COOH and —COO—$(C_1-C_6)$alkyl,
(d) aryl $C_1-C_6$ alkyl carbonyl, wherein aryl represents phenyl, pyridyl, thienyl or furanyl, optionally substituted by one or more substituents selected from the group consisting of $C_1-C_6$ alkyl, $C_1-C_6$ alkoxy, —COOH and —COO—$(C_1-C_6)$alkyl,
(e) $C_1-C_6$ alkoxy $C_1-C_6$ alkyl carbonyl,
(f) $C_1-C_6$ alkoxy carbonyl,
(g) aryl carbonyl, wherein aryl represents phenyl, pyridyl, thienyl or furanyl, optionally substituted by one or more substituents selected from the group consisting of $C_1-C_6$ alkyl, $C_1-C_6$ alkoxy, —COOH and —COO—$(C_1-C_6)$alkyl,
(h) $C_3-C_7$ cycloalkyl $C_1-C_6$ alkylcarbonyl, wherein the cycloalkyl group is optionally substituted by one or more substituents selected from the group consisting of $C_1-C_6$ alkyl, $C_1-C_6$ alkoxy, —COOH and —COO—$(C_1-C_6)$alkyl,
(i) $C_1-C_6$ alkoxy $C_1-C_6$ alkoxycarbonyl,
(j) $C_1-C_6$ alkoxy $C_1-C_6$ alkoxy $C_1-C_6$ alkylcarbonyl,
(k) a carbamoyl group with the formula

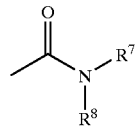

wherein $R^7$ and $R^8$ are the same or different and are H or $C_1-C_6$ alkyl,
(l) $R^9$—$(C_1-C_6)$alkylcarbonyl,
wherein $R^9$ is selected from the group consisting of HOC=O—, $C_1-C_6$ alkyl-O—C=O—, and an amino group with the formula

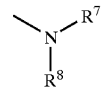

wherein $R^7$ and $R^8$ are the same or different and are H or $C_1-C_6$ alkyl,
(m) $R^9$-hydroxylated-$(C_1-C_6)$alkylcarbonyl, and
(n) $R^9$—$(C_1-C_6)$ alkenylcarbonyl; and
X is selected from the group consisting of:
(a) NH and
(b) O.

2. The compound according to claim 1, or a pharmaceutically acceptable salt thereof, wherein:
$R^1$ is selected from the group consisting of:
(a) $CH_3$ and
(b) $CH_2OH$;
$R^2$ is $C_1-C_6$ alkyl;
$R^3$ is $C_1-C_6$ alkyl;
$R^4$ is selected from the group consisting of:
(a) H and
(b) halogen;
$R^5$ is selected from the group consisting of:
(a) H and
(b) $C_1-C_6$ alkyl;
$R^6$ is selected from the group consisting of:
(a) $C_1-C_6$ alkyl carbonyl,
(b) $C_3-C_7$ cycloalkyl carbonyl, wherein the cycloalkyl group is optionally substituted by one or more substituents selected from the group consisting of $C_1-C_6$ alkyl, $C_1-C_6$ alkoxy, —COOH and —COO—$(C_1-C_6)$alkyl,
(c) aryl $C_1-C_6$ alkyl carbonyl, wherein aryl represents phenyl, pyridyl, thienyl or furanyl, optionally substituted by one or more substituents selected from the group consisting of $C_1-C_6$ alkyl, $C_1-C_6$ alkoxy, —COOH and —COO—$(C_1-C_6)$alkyl,
(d) $C_1-C_6$ alkoxy $C_1-C_6$ alkyl carbonyl,
(e) $C_1-C_6$ alkoxy carbonyl,
(f) aryl carbonyl, wherein aryl represents phenyl, pyridyl, thienyl or furanyl, optionally substituted by one or more substituents selected from the group consisting of $C_1-C_6$ alkyl, $C_1-C_6$ alkoxy, —COOH and —COO—$(C_1-C_6)$alkyl,
(g) $C_3-C_7$ cycloalkyl $C_1-C_6$ alkylcarbonyl, wherein the cycloalkyl group is optionally substituted by one or more substituents selected from the group consisting of $C_1-C_6$ alkyl, $C_1-C_6$ alkoxy, —COOH and —COO—$(C_1-C_6)$alkyl, (h) $C_1$–$C_6$ alkoxy $C_1$–$C_6$ alkoxycarbonyl,
(i) $C_1$–$C_6$ alkoxy $C_1$–$C_6$ alkoxy $C_1$–$C_6$ alkylcarbonyl,
(j) a carbamoyl group with the formula

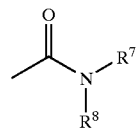

wherein $R^7$ and $R^8$ are the same or different and are H or $C_1$–$C_6$ alkyl,
(k) $R^9$—($C_1$–$C_6$)alkylcarbonyl,
wherein $R^9$ is selected from the group consisting of HOC=O—, $C_1$–$C_6$ alkyl-O—C=O—, and an amino group with the formula

wherein $R^7$ and $R^8$ are the same or different and are H or $C_1$–$C_6$ alkyl,
(l) $R^9$-hydroxylated-($C_1$–$C_6$)alkylcarbonyl, and
(m) $R^9$—($C_1$–$C_6$) alkenylcarbonyl; and X is selected from the group consisting of:
(a) NH and
(b) O.

3. The compound according to claim 1, or a pharmaceutically acceptable salt thereof, wherein $R^1$ is $CH_3$ or $CH_2OH$;
$R^2$ is $CH_3$ or $CH_2CH_3$;
$R^3$ is $CH_3$ or $CH_2CH_3$;
$R^4$ is H, Br, Cl or F; and
$R^5$ is H or $CH_3$.

4. A compound selected from the group consisting of:
8-(2,6-dimethylbenzylamino)-2,3-dihydroxymethyl-imidazo[1,2-a]pyridine;
8-(2-ethyl-6-methylbenzylamino)-2-hydroxymethyl-3-methylimidazo[1,2-a]pyridine;
8-(2,6-dimethylbenzylamino)-2-hydroxymethyl-3-methylimidazo[1,2-a]pyridine;
8-(2,6-dimethylbenzylamino)-3,6-dimethyl-2-hydroxymethylimidazo[1,2-a]pyridine;
[8-(2,6-dimethylbenzylamino)-3-methylimidazo[1,2-a]pyridin-2-yl]methyl acetate;
[8-(2,6-dimethylbenzylamino)-3-methylimidazo[1,2-a]pyridin-2-yl]methyl ethyl carbonate;
[8-(2,6-dimethylbenzylamino)-3-methylimidazo[1,2-a]pyridin-2-yl]methyl N,N-dimethylcarbamate;
1-[[8-(2,6-dimethylbenzylamino)-3-methylimidazo[1,2-a]pyridin-2-yl]methyl]3-ethyl malonate;
4-[[8-(2,6-dimethylbenzylamino)-3-methylimidazo[1,2-a]pyridin-2-yl]methoxy]-4-oxobutanoic acid;
4-[[8-(2-ethyl-6-methylbenzylamino)-3-methylimidazo[1,2-a]pyridin-2-yl]methoxy]-4-oxobutanoic acid,
5-[[8-(2,6-dimethylbenzylamino)-3-methylimidazo[1,2-a]pyridin-2-yl]methoxy]-5-oxopentanoic acid;
[8-(2,6-dimethylbenzylamino)-3-methylimidazo[1,2-a]pyridin-2-yl]methyl 2-(dimethylamino)acetate;
or a pharmaceutically acceptable salt thereof.

5. A pharmaceutical composition comprising a compound according to any one of claims 1–4 and at least one antimicrobial agent for simultaneous, separate or sequential administration in the treatment of gastrointestinal inflammatory diseases.

6. A pharmaceutical composition comprising a compound according to any one of claims 1–4 and at least one proton pump inhibitor for simultaneous, separate or sequential administration in the treatment of gastrointestinal inflammatory diseases.

7. A process for the preparation of a compound according to claim 1, comprising:

a) reacting a compound of Formula III

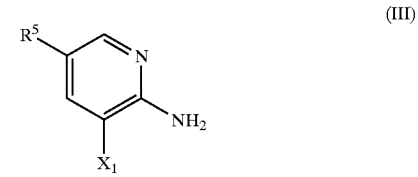

wherein $X_1$ is $NH_2$ or OH, and $R^5$ is as defined in claim 1, with a compound of Formula IV

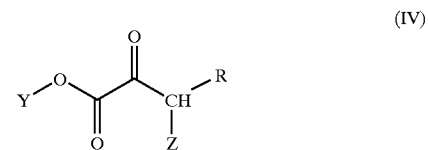

wherein Z is a leaving group, Y is a lower alkyl group and R is selected from the group consisting of H, $CH_3$ and an ester group selected from the group consisting of $COOCH_3$ and $COOC_2H_5$, in an inert solvent under standard conditions to yield a compound of Formula II;

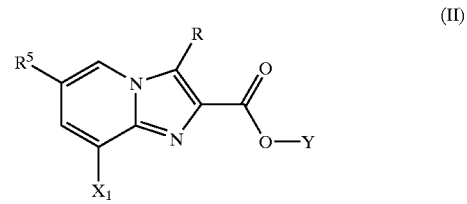

b) reacting a compound of Formula V

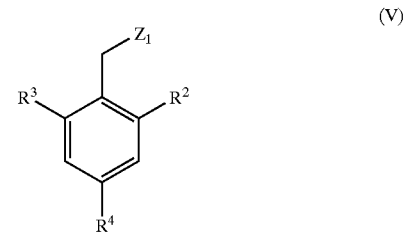

wherein $R^2$, $R^3$ and $R^4$ are as defined in claim 1 and $Z_1$ is a leaving group, with the compound of Formula II under standard conditions in an inert solvent with or without a base, to yield a compound of Formula VI,

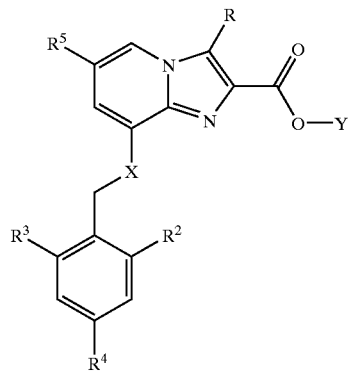

(VI)

wherein $R^2$, $R^3$, $R^4$, $R^5$ and X are as defined in claim 1, Y is a lower alkyl group and R is selected from the group consisting of H, $CH_3$, and an ester selected from the group consisting of $COOCH_3$ and $COO_2H_5$ group; and c1) when $R^6$ of Formula I is H, reducing the compound of Formula VI in an inert solvent to yield a compound of Formula I wherein $R^6$ is H; or c2) when $R^6$ of Formula I is not H, introducing substituent $R^6$ by standard acylating procedures by reacting a compound of Formula I wherein $R^6$ is H, with the acid, acid halide or the anhydride of $R^6$ to yield a compound of Formula I when $R^6$ is not H.

8. A process for the preparation of a compound according to claims 1 wherein $R^6$ is not H comprising:

a) halogenation of the hydroxymethyl group in a compound of Formula I when $R^6$ is H to the corresponding halogenmethyl group of Formula VII by standard methods, and

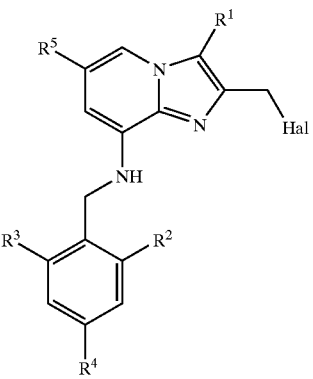

(VII)

b) introducing substituent $R^6$ of Formula I by reacting the compound of Formula VII with the corresponding acid of $R^6$ ($R^6 \neq OH$) under standard conditions.

9. A pharmaceutical formulation comprising a compound according to any one of claims 1 to 4 as active ingredient in combination with a pharmaceutically acceptable diluent or carrier.

10. A method for inhibiting gastric acid secretion comprising administering to a mammal in need of such inhibition an effective amount of a compound according to any one of claims 1 to 4.

11. A method for the treatment of gastrointestinal inflammatory diseases comprising administering to a mammal in need of such treatment an effective amount of a compound according to any one of claims 1 to 4.

12. A method for the treatment of conditions involving infection by *Helicobacter pylori* of human gastric mucosa, comprising administering to a mammal in need of such treatment an effective amount of a compound as claimed in any one of claims 1 to 4 in combination with at least one antimicrobial agent.

13. The pharmaceutical formulation of claim 9 further comprising at least one antimicrobial agent.

* * * * *

UNITED STATES PATENT AND TRADEMARK OFFICE
CERTIFICATE OF CORRECTION

PATENT NO. : 6,613,775 B1  Page 1 of 1
DATED : September 2, 2003
INVENTOR(S) : Amin et al.

It is certified that error appears in the above-identified patent and that said Letters Patent is hereby corrected as shown below:

Column 4,
Line 12, delete "methyl]3-ethyl" and substitute therefor -- methyl] 3-ethyl --.

Column 15,
Line 19, insert -- and -- after "combined --.

Column 21,
Line 57, delete "methyl]3-ethyl" and substitute therefor -- methyl] 3-ethyl --.

Column 24,
Line 21, delete "$R^6 \neq OH$" and substitute therefor -- $R^6 \neq H$ --.

Signed and Sealed this

Thirteenth Day of January, 2004

JON W. DUDAS
*Acting Director of the United States Patent and Trademark Office*